United States Patent
Cohen et al.

[19]

[11] Patent Number: 6,146,423
[45] Date of Patent: Nov. 14, 2000

[54] PATELLA REPLACEMENT APPARATUS

[75] Inventors: Robert C. Cohen, Rockaway Township; Rafail Zubok, Midland Park; Christopher G. Sidebotham, Randolph, all of N.J.

[73] Assignee: Implex Corporation, Allendale, N.J.

[21] Appl. No.: 09/239,467

[22] Filed: Jan. 28, 1999

[51] Int. Cl.[7] ................................................. A61F 2/38
[52] U.S. Cl. ........................................................ 623/20.2
[58] Field of Search ........................... 623/18, 20, 20.18, 623/20.2

[56] References Cited

U.S. PATENT DOCUMENTS

| | | |
|---|---|---|
| 4,007,495 | 2/1977 | Frazier . |
| 4,041,550 | 8/1977 | Frazier . |
| 5,019,104 | 5/1991 | Whiteside et al. . |
| 5,314,480 | 5/1994 | Elloy et al. . |
| 5,383,937 | 1/1995 | Mikhail ........................................ 623/20 |
| 5,425,775 | 6/1995 | Kovacevic et al. . |
| 5,593,450 | 1/1997 | Scott et al. ................................. 623/20 |
| 5,702,465 | 12/1997 | Burkinshaw ................................ 623/20 |
| 5,723,016 | 3/1998 | Minns et al. ................................ 623/20 |
| 5,871,540 | 2/1999 | Weissman et al. ......................... 623/20 |
| 5,938,698 | 8/1999 | Sandoz et al. ............................. 623/11 |

OTHER PUBLICATIONS

Nontraumatic Bone and Joint Disorders, pp. 2026–2027.
Fractures of Lower Extremity, pp. 841–847.
Patellectomy and Reconstructive Surgery for Disorders of the Petellofemoral Joint, Setion VI: The Knee, pp. 1688–1696.

*Primary Examiner*—David H. Willse
*Assistant Examiner*—Suzette J. Jackson
*Attorney, Agent, or Firm*—Arthur L. Plevy; Buchanan Ingersoll PC

[57] ABSTRACT

A patella replacement device consists of a porous metal insert which is surrounded by a metallic ring which is press-fit to a portion of the insert. The porous insert has cement accommodating apertures. A polyethylene device or biocompatible articulating material has projections which fit into the apertures in the porous insert and the combination is used for the repair or replacement of the patella bone. The porous metal insert consists of a high porosity metal material for initial stability through the adhesive and frictional properties of the metal material and allows for articulation of one polyethylene or metal bearing surface to a normal non-resurfaced femur or a femur that has been resurfaced with a prosthetic replacement device.

24 Claims, 5 Drawing Sheets

KNEE AREA

PATELLA REPLACEMENT APPARATUS

This invention relates to a patella replacement apparatus and more particularly to an improved patella prosthesis allowing improved biological fixation to the patella knee area of a patient user.

BACKGROUND OF THE INVENTION

Patella injuries and complications from previous procedures are extremely difficult for the orthopedic surgeon to manage such procedures and have a limited success towards maintaining the patient's full function of the knee joint. Many different problems leave the surgeon with limited options. These problems can directly or indirectly result from trauma, chronic pain, or loss of bone due to a previous procedure, like a total knee replacement, where the patellar component loosened, became infected, or was painful. Often the complete patellar bone is removed or, in cases of a failed patellar resurfacing component, the bone loss are substantial and complications from subsequent procedures is relatively high. Loss of the patellar bone and the resulting loss of soft tissue balancing and tensioning compromises strength and articulation of the knee joint, and the patient's quality of life.

The prior art is cognizant of many different prosthetic devices for the replacement of the articulating surface of the patella commonly referred to as the knee cap. These devices have been designed for implantation in many cases where replacement of the articulating surface of the patella is indicated. There are many examples of such devices in the prior art and there are many devices which are commercially available to surgeons. One example of such a device can be had by reference to U.S. Pat. No. 5,019,104, entitled Patella Prosthesis and Method of Making the Same issued on May 28, 1991 to Leo A. Whiteside, et al. and assigned to Dow Coming Wright Corporation.

This patent discusses prior art devices in the background of the invention. Another patella replacement apparatus can be found in U.S. Pat. No. 4,007,495 entitled Patella Femoral Prosthesis which shows a device consisting of two components: a patella prosthesis and a femoral prosthesis, which are connected to each other. The femoral prosthesis is formed of steel and is attached by bone cement. The patella prosthesis is formed of polyethylene or a similar plastic material. The femoral prosthesis is mounted on the femur and the patella prosthesis is mounted on the patella. They are connected together by pressing the patella and the patella prosthesis towards the femoral prosthesis through a pin and slot arrangement.

U.S. Pat. No. 5,314,480 entitled Patella Components issued on May 24, 1994 and shows a patella replacement using a femoral component and a tibial component including a metal disk imbedded within a high molecular polyethylene disk. The polyethylene disk surrounds the edge of the metal disk so that the metal disk is flush with the polyethylene disk on one surface. The metal disk is provided with serrations which fit into the polyethylene disk to prevent rotation.

Patellar devices of various types and configurations have been utilized over the years to address the revision prosthetic patient and the complete patellectomy patient. For the patellectomy patient, the device must be able to fix biologically to remnant bone or soft tissue such as muscle or tendons. Additionally, the device must articulate and function within the confines of the cartilage on the femoral bone. The survivorship rate of devices that attempted to replace the patella has been poor and surgeons typically choose to remove the total patellar bone, leaving the patient with a compromised knee joint. Removal of the patellar bone creates about a 20% loss of the quadriceps mechanism muscle strength. Research has concluded that many patients only regain about 75% of their knee normal strength. For the case of removal of a failed prosthetic patellar component from a total knee joint replacement procedure, the amount of cancellous bone remaining is minimal and offers the surgeon a challenge for the new implant stability and long term fixation, while attempting to provide biomechancial articulation against the existing femoral component. The incidence of pain, lack of full function, and rate of component loosening is unacceptably high.

It is therefore an object of the present invention to provide an improved patella replacement device. The improved device as will be explained, can restore or mimic the biomedical function of the normal patella bone in severe cases. In this manner, the replacement by the patella replacement device of this invention results in an improved operation and improved muscle use for the patient. The device is simple to install as compared to prior art devices and offers advantages both to the surgeon and to the patient.

SUMMARY OF THE INVENTION

A patella replacement device for use in repairing or replacing the destroyed natural patella of a patient, comprising: a first member fabricated from a porous metal material and having a rounded fixation surface for implantation within the patella region of a patient with said porous metal allowing biological fixation to said patella region of said patient, said first member having a relatively flat surface opposite said rounded surface and having at least one aperture therein; a second member fabricated from a biocompatible material and having a top rounded surface and an opposing surface having an extending projection for coacting with said aperture to enable said first member to couple to said second member with said second member operative to allow articulation against the femoral area of said patient.

DETAILED DESCRIPTION OF THE FIGURES

Figure 1:
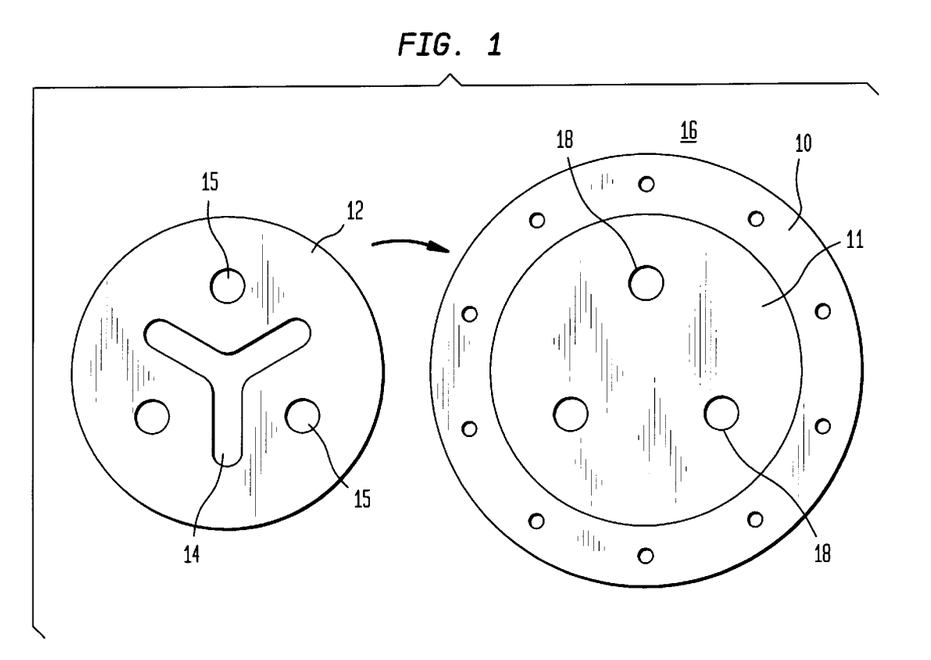
FIG. 1 depicts a patella replacement device according to this invention and shows the two components of the device.

Referring to FIG. 1 there is shown the patella knee replacement device which consists of two components. The second component 12 is a bearing component which desirably is fabricated from polyethylene and has a rounded top surface which will be further described. The first component is a patella assembly 16, which has a central porous metal section 1 surrounded by an annular metal ring 10, as will be explained.

The bottom surface of the polyethylene bearing component 12 has a Y-shaped slot 14 which is centrally located between three upstanding posts each designated by the same reference numeral 15. The Y-slot 14 is used to accommodate bone cement during implantation of the device. The posts 15 are inserted into apertures 18 of the component 16 which consists of the central base member 11 fabricated from a porous material. The porous material is sold under the trademark HEDROCEL as provided by the Implex Corp. of Allendale, N.J., the Assignee herein. As will be explained, the HEDROCEL material is a metallic porous metal material which allows for bone or soft tissue ingrowth and is widely used by Implex in prosthetic devices. Coupled to the HEDROCEL base unit 11 is a outer metal ring 10. Ring 10 is preferably fabricated from titanium. It is an solid titanium ring that provides an interference fit with the HEDROCEL base. An interference fit can be implemented between the two units by many conventional techniques. As can be seen from FIG. 1, the posts 15 associated with the polyethylene bearing unit 12 are inserted into the apertures 18 which are formed in the HEDROCEL base unit 11. The holes 18 can also accommodate a bone cement employed during the operation. The surgeon actually receives as a patella replacement the base unit 16 and the polyethylene bearing component 12. These components are secured together during the surgical procedure by the surgeon to replace the patella. A complete description of the HEDROCEL material which basically is a porous tantalum material can be had by reference to a co-pending application assigned to the Assignee herein, namely, Implex Corporation. The co-pending application was filed on Oct. 26, 1998 as Ser. No. 09/179,119 and is entitled: Bonding of Porous Materials to Other Materials Utilizing Chemical Vapor Deposition. That application describes in detail the structure of HEDROCEL cellular structure biomaterial which is employed in prosthetic devices as implemented by the Assignee herein, Implex Corp. And is incorporated herein by reference.

Figure 2:
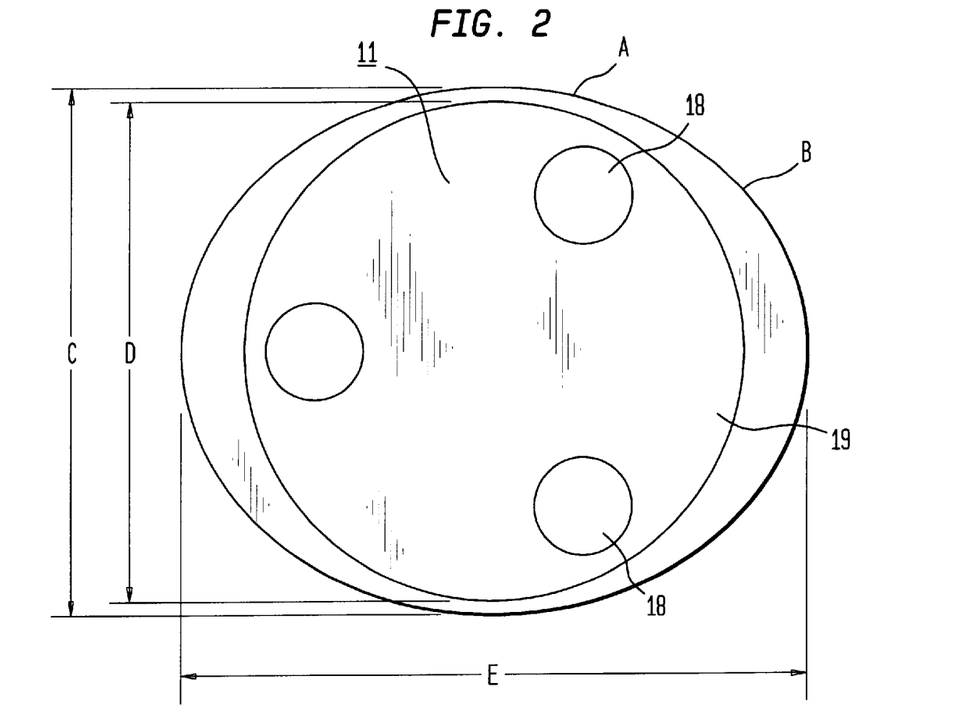
FIG. 2 depicts a top view of the HEDROCEL patella insert, including the mating apertures.

Referring to FIG. 2, there is shown a top view of the HEDROCEL patella insert 11 of FIG. 1. FIG. 2 shows the HEDROCEL insert 11 on an enlarged scale. The same reference numerals have been employed to describe the basic structure. As seen from the top view of FIG. 2, the HEDROCEL has three apertures 18, which as was explained, coact with the posts of the polyethylene member and are filled with a suitable cement or adhesive during a surgical procedure. As seen, the entire unit of FIG. 2 is fabricated from HEDROCEL biocompatible metal material which has been described above.

Figure 3:
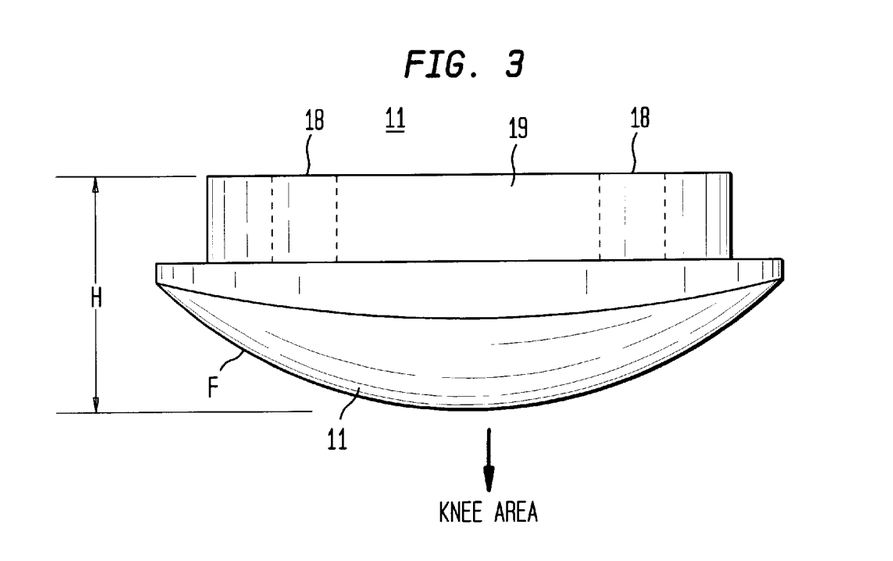
FIG. 3 shows a side view of the patella insert according to FIG. 2.

FIG. 3 shows a side view of the patella insert unit 11 of FIG. 2. As can be seen from FIGS. 2 and 3, the patella insert unit 11 contains various reference letters such as A, B, C, E, F, and H. These letters represent different dimensions which are necessary to accommodate different sized individuals. As is well-known, all individuals are not the same size and not the same weight, and, therefore, in order to provide a complete range of patella replacement devices, one needs to accommodate men, women, and children of various sizes. Therefore, the dimensions will vary accordingly. In any event, in order to gain some typical insight to the dimensions shown on FIGS. 2 and 3, the following values are indicated. For small sizes, the A Radius is 0.632 inches. The B Radius is 0.449 inches. The C Radius is typically 0.958 inches. The E Radius, which is shown in FIG. 2, is typically 1.099 inches and the D Radius, also shown in FIG. 2, is typically 0.918 inches for a small individual. The dimension H of FIG. 3 varies from 0.276 inches to 0.709 inches to allow for different knee configurations. The spherical radius F varies from 1.299 to 0.553 inches. These dimensions may vary between the two limits to provide twelve different dimensioned devices as between H and F for small sized individuals. For a medium individual, A would be 0.709 inches, B is 0.502 inches, C is 1.063 inches, E. is 1.218 inches, and D. is 1.023 inches. The dimension H again varies between 0.276 to 0.799 with the dimension F varying between 1.614 to 0.593 from the smallest to largest of the medium size. For a large individual, the dimensions in inches would be A, 0.784, B, 0.555, C, 1.169, E, 1.336, and D, 1.129. For an extra large individual, the dimensions in inches A equals 0.862, B is 0.607, C is 1.274, E is 1.454, and D is 1.234. In FIG. 3, the dimension H varies between 0.276 inches to 0.709 inches which essentially is the variation in height, again depending on the size of the small individual. As shown in FIG. 3, the spherical radius F of the top surface also varies for small and large individuals. The maximum spherical radius F would be 2.244 inches for an extra large individual to a smallest radius of 0.553 inches for a small individual. Atypical average spherical radius F for a medium-sized individual would be about 1 inch. As one can see, the entire HEDROCEL unit is relatively small and, for example, the overall diameter E varies from a minimum of 1.099 inches for a small individual to a maximum of 1.454 inches for an extra large individual. The radius C varies from 0.958 inches for a small individual to 1.274 inches for a very large individual and so on. The position of the holes 18 as well as the diameters of the same are as indicated in the Figures. These dimensions do not vary, but are maintained relatively constant. As seen in FIG. 3, the HEDROCEL patella insert 11 has a curved outer surface or dome designated by the spherical radius F and has an extending inner circular portion 19 with a relatively flat top surface. The unit has a shape to conform to the patella of a typical user and as indicated, a surgeon would measure the patient's knee area and select a suitable patella insert according to the dimensions given above.

Figure 4:
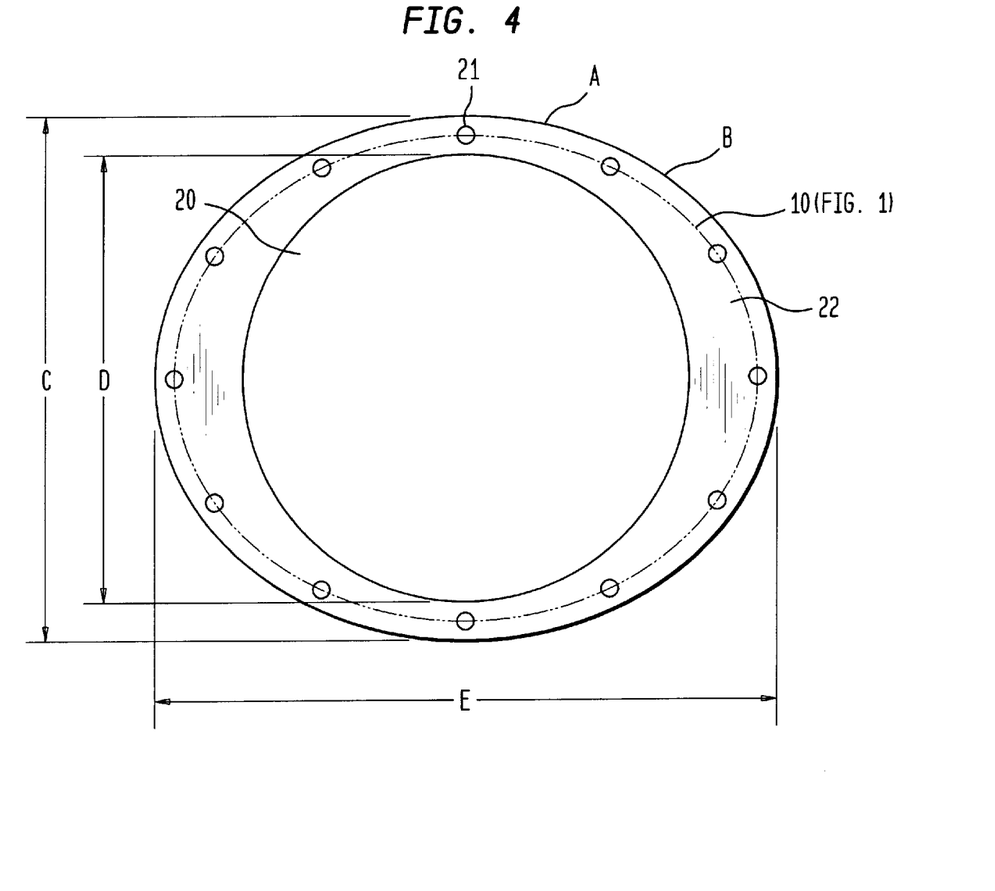
FIG. 4 shows a top view of a patella ring utilized in this invention.
Figure 5:
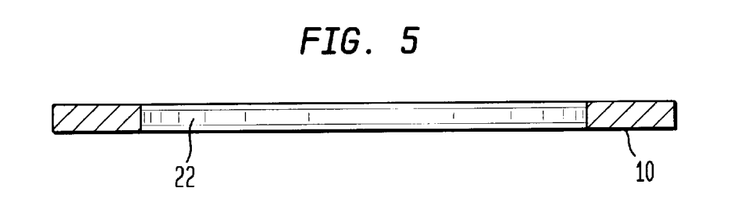
FIG. 5 shows a cross-sectional view of the ring of FIG. 4.

Referring to FIG. 4, there is shown a top view of the patella ring which is depicted in FIG. 1 by reference numeral 10. The patella ring is an annular ring and has a central aperture 20 which is of a diameter slightly less than the extending central flange portion 19 of the HEDROCEL patella insert 11 of FIG. 3. In this manner, the ring is force-fit over the region 19 of the patella assembly by means of a press or a clamping system where the ring is held over the area 19 of the patella insert and is pushed or clamped to provide an interference bond or fit. To provide an interference fit, the diameter of the aperture 20 is between one and four thousandths of an inch less than the diameter of the area 19 (D of FIG. 2). The ring also has an inner peripheral groove 22 which enables the force-fit to more easily occur during the clamping procedure. The ring 10 is fabricated from a suitable biocompatible metal such as titanium or tantalum and essentially has a series of apertures 21 around the peripheral edge. The apertures 21 enable a physician to apply sutures to secure the ring and the patella insert to the knee area of a patient as will be subsequently explained. Again, because of the dimensions of different people, the ring is associated with dimensions which include the A Radius, the B Radius, and dimensions C, B and E. These dimensions for a small person to an extra large person vary. For example, dimension A can vary from 0.732 to 0.962 inches. Radius B varies from 0.549 for a small to 0.707 inches for an extra large person. Radius C varies from 1.158 to 1.474 inches for small to extra large. Dimension E varies from 1.299 to 1.654 inches for small to extra large. The dimensions indicated as D vary from 0.914 for small to 1.230 for a large person. Thus, as one can ascertain, the ring particularly Dimension D which is the inner open area 20 of the annular ring or patella ring 10, varies from 0.194 to 1.230 for small to extra large. The diameter 20 is preferably four one-thousandths smaller than the diameter D of the patella insert 11.

Figure 6:
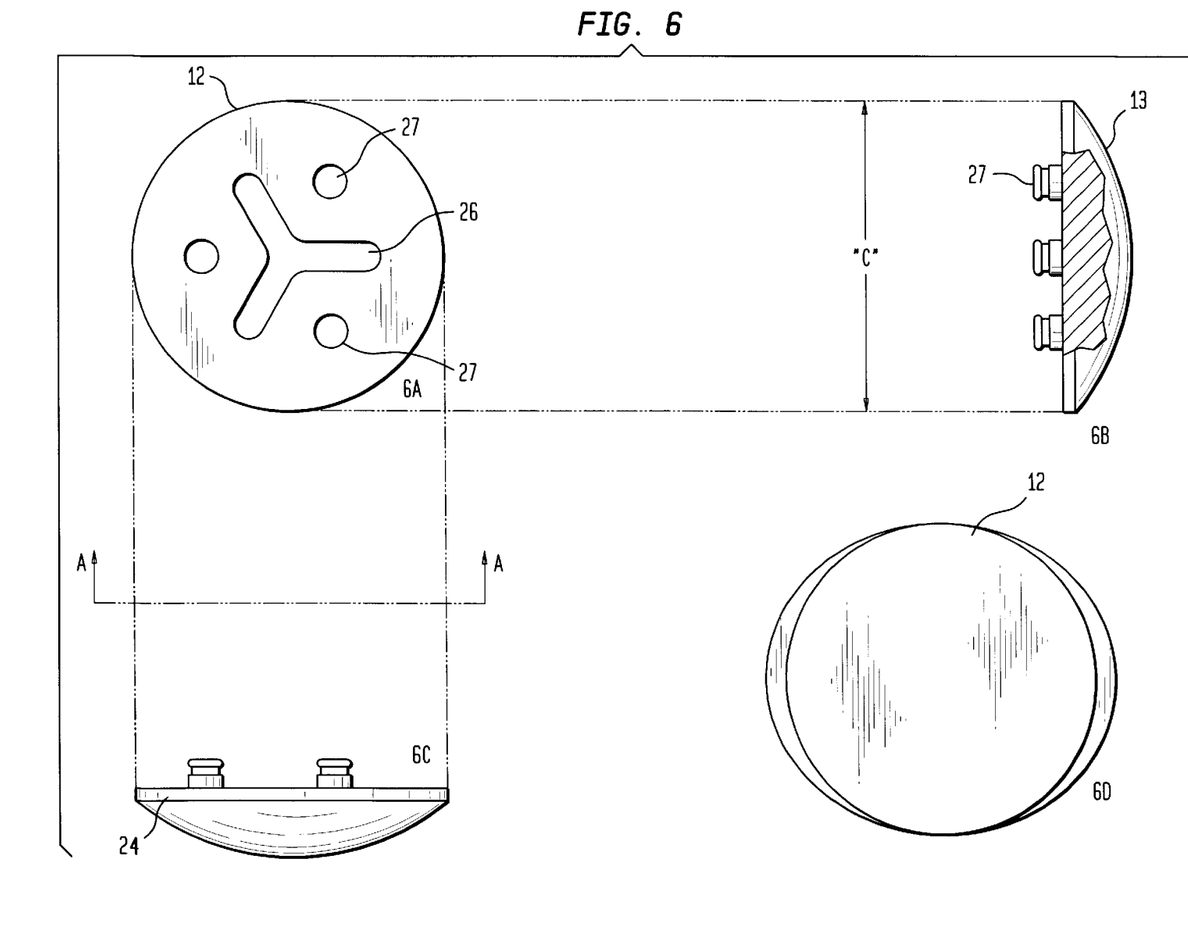
FIG. 6A is a top view of the polyethylene patella device.
FIG. 6B shows a side view of the device.
FIG. 6C shows a side view of the device from a different perspective.
FIG. 6D shows a top view of the device.

FIGS. 6A, 6B, and 6C show different views of the polyethylene patella insert which is depicted in FIG. 1 as 12. The insert 12 is fabricated from polyethylene and has a smooth rounded outer surface or dome 13 (6B) with a peripheral flat edge 24 (6C) The top has a Y-shaped slot 26 with three upstanding projections or posts 27. The Y-shaped slot accommodates bone cement. The top view of the insert is shown in FIG. 6D. The insert has a smooth rounded top surface 12 which is the outer surface of the device. As indicated, the patella polyethylene member 12 has three posts designed by reference numeral 27. Each of the posts has a unique configuration with a large top, a recessed middle, and a larger bottom. This is to enable the posts to be inserted into the apertures of the HEDROCEL patella replacement device and be secured in place by the means of a suitable biocompatible adhesive, glue or cement which is inserted in the apertures of the HEDROCEL insert by the surgeon. This, in fact, will position the polyethylene cover member into the HEDROCEL insert which enables the entire assembly to be connected together. In a similar manner, the polyethylene patella device 12 has varying dimensions depending on the size of a patient and the radii are again indicated on the drawing with the A radius varying from 0.732 inches to 0.962 from small to extra large. The dimension C varies from 1.158 inches to 1.474 inches from small to extra large and the dimension D varies from 1.299 inches to 1.654 inches from small to extra large. It is again noted that the assembly as it reaches the physician, consists of the ring together with the HEDROCEL patella replacement member assembled as a single unit with the ring force-fitted over the HEDROCEL member. The polyethylene section shown in FIGS. 6A, 6B and 6C is separately supplied. All the units are ordered by the physician or the surgeon after measurements are made considering the size of the patient's knee and of course, considering the size and weight of the patient.

Figure 7A:
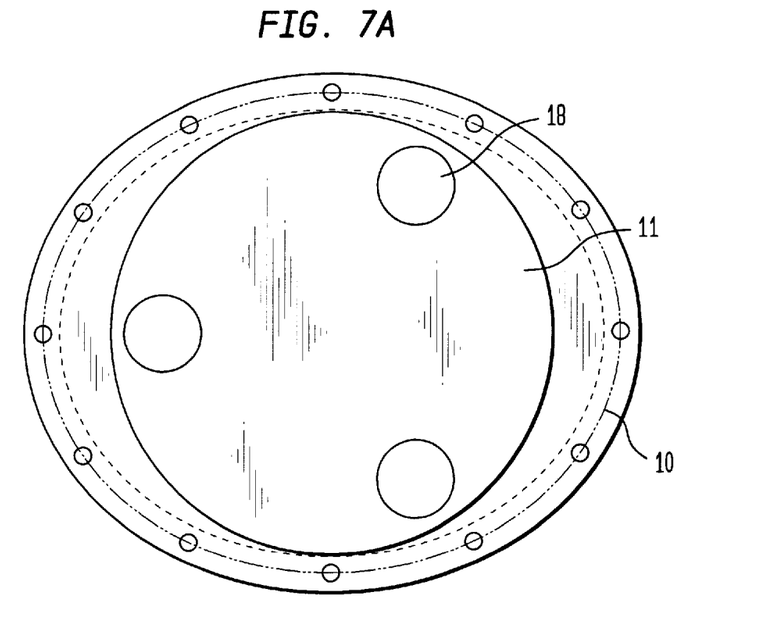
FIG. 7A shows a top view of the assembled ring and patella insert.
Figure 7B:
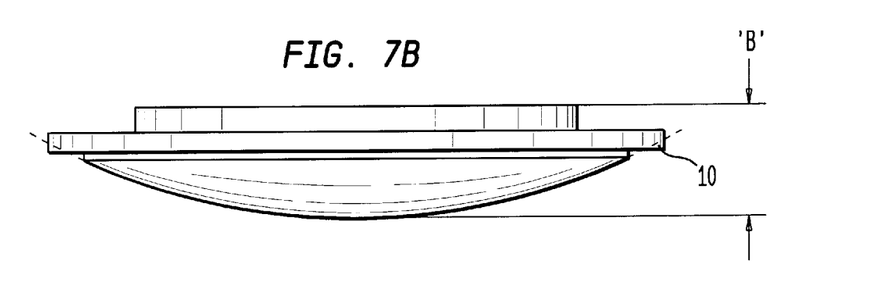
FIG. 7B shows a side view of the patella ring and insert.

Referring to FIG. 7A, there is shown a top view of the assembled unit which consists of the HEDROCEL patella unit 11 having the ring 10 secured thereto. FIG. 7B clearly shows the assembly with the ring 10 secured thereto. It is indicated that this unit comes together with the plastic assembly for placement by a surgeon on the knee area of a patient. It is again understood that the ring 10 is press-fitted onto the HEDROCEL member. One will understand that the assembly shown in FIGS. 7A and 7B comes in various sizes (as indicated above) depending on the size of a patient as from small to extra large.

Figure 8:
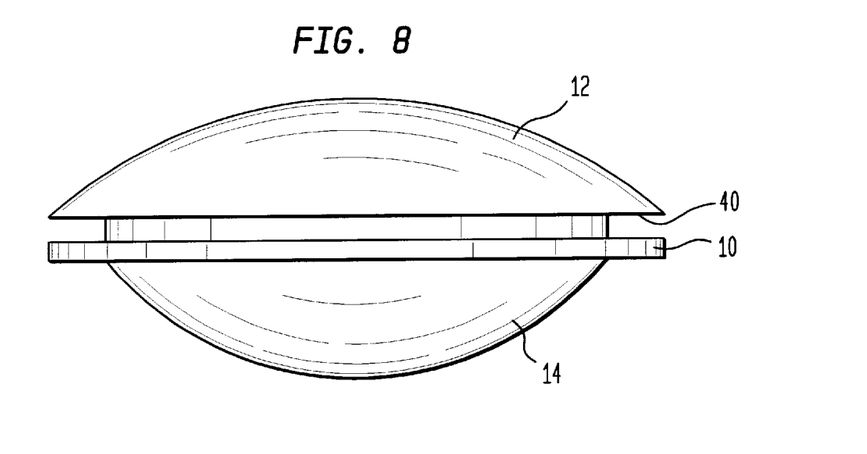
FIG. 8 shows a side view of the polyethylene patella device inserted into the HEDROCEL patella insert.

Referring to FIG. 8, there is shown the assembled base unit 11 connected to the polyethylene assembly 12. As indicated, the upstanding posts 15 of the polyethylene unit 12 are inserted onto the apertures 18 of the HEDROCEL base unit 11. Based on the dimensions of the apertures 18 and the post 15, there is a peripheral gap 40 formed when such insertion occurs. This peripheral gap 40 enables the surgeon to wrap soft tissue in the gap to further secure the prosthetic device and to assure optimum coupling to the knee area.

The flexibility of the HEDROCEL assembly 11 gives great advantages to the entire structure, thereby enabling a surgeon to implant this device with the HEDROCEL section 11 promoting bone and/or soft tissue growth and promoting better security. The smooth top surface or dome of the HEDROCEL unit is placed against the knee area of the patient (FIG. 3). The titanium ring serves as a holding device as well as enabling the patient to receive sutures and to have the device implanted upon the patient's knee. The polyethylene member acts as an articulator surface against the patient's cartilage or prosthetic femoral replacement enabling the patient to resume normal activities and be pain free. The device has great utility and is believed to be superior in operation than prior art devices because of the structure as described above. In order to fully understand the emplacement of the device, the following discussion is applicable.

Of course, as indicated a main use of the device is the fact that the device can restore or mimic the biomechanical function of the normal patella bone in severe revision or bone replacement cases which is a major problem in regard to prior art devices. Essentially, a device must be looked at for serving two subgroups with severe patella problems. First, there is a group of patients who exist with bone remaining. More descriptively, the remnants of bone or fragments of bone may remain attached to the soft tissue after extreme trauma or removal of a previously implanted primary surgery patella resurfacing component. Because in total knee replacement reconstruction, a patella articulating side only prosthetic is either implanted with cement or cement-less; but, regardless when these patellae get revised because of pain or loosening, much of the cancellous bone within the patella itself is also removed. Little structural bone remains to secure another primary-type implant. This is a main advantage of using the present invention. Secondly, in a small percentage of the population, people suffer from chronic patella pain. Often the cause remains undiscovered, but removal of the patella bone offers relief. Unfortunately, for the patient, this will also sacrifice a certain amount of leg strength. Therefore, in the present device, the HEDROCEL portion will allow the biological fixation to soft tissue (muscles or tendons) and/or the bone (remaining fragments from the original patella bone). The polyethylene or solid metal articulating side must allow articulation against the normal cartilage of the femur, or, in cases of a total knee revision, articulation against the metal of the prosthetic femoral component. As indicated above, the embodiments are shown and typical dimensions are given. The base unit which is shown in FIG. 2 or 3 is made of HEDROCEL and has a factory assembled titanium solid ring that is interference fit to the base. The articulating portion is an all-polyethylene patella resurfacing component which is utilized in total knee joint replacement.

The operating procedure is as follows: The unit assembly will function if a patella bone is completely removed from a patient or, the patella fragments that still remain to the soft tissue post trauma are exposed and the loose fragments are removed; or, the primary patella component that failed is removed and a remaining patella bone shell is prepared to accept the device. The appropriate size HEDROCEL base with ring is placed dome-side to the soft tissue or remaining bone. The adhesive and frictional surface characteristic properties of the HEDROCEL unit will initially hold (similar to velcro) the component in place. The holes in the titanium ring allow for adjunct sutures that can further hold the component either to the soft tissue or bone. A solid metal ring is used instead of HEDROCEL alone so that the sutures do not abrade from repetitive motion and break. After the base is stable, trial polyethylene components will fit into the three holes in the HEDROCEL. Trial articulation against the femur with the whole knee flexing and extending will be performed and patella tracking and joint tensioning is assessed. The implantable polyethylene patella component is then cemented into place. An option exists to allow implantation of a solid metal component which may be preferred for articulation against femoral cartilage. The bone cement, (standard in hospital operating rooms) is placed in the three holes and in the Y-shaped aperture and the poly component is pushed into the holes. The surgeon holds the polycomponent against the HEDROCEL base until the cement is cured and hardened. The joint is reduced. The device, therefore, has many uses and many novelties, and essentially, depicts a metal or metal and polyethylene device which can be optimally utilized for the repair or replacement of the patella bone and which device uses a high porosity metal material for initial stability through the adhesive and frictional properties of the metal material and allows for articulation of a polyethylene or metal bearing surface to a normal resurfaced femur or a femur that has been resurfaced with a prosthetic replacement device therein.

It is, of course, understood that the above described embodiments represent the preferred device as presently understood by the inventors herein. In any event, many substitutes can be implemented without departing from the spirit and scope of this invention. Such substitutes are alternatives involving fabrication of the metal ring which can be made from other materials. It is also understood that one skilled in the art could fabricate a metal ring as an integral portion of the HEDROCEL base unit. One can also utilize different types of porous materials to mimic the device depicted above without departing from the spirit and scope of this invention, and all such alternatives are considered to be part of this invention.

What is claimed is:

1. A patella replacement device for use in repairing or replacing the destroyed natural patella of a patient, comprising:

a first member fabricated from a biocompatible porous metal material and having a rounded fixation surface for implantation in the patella region of a patient with said porous metal allowing biological fixation to said patella region of said patient, said first member having a relatively flat surface opposite said rounded surface and having at least one aperture therein;

a second member fabricated from a biocompatible joint articulating material and having a top rounded surface and an opposing surface having an extending projection for coacting with said aperture to enable said first member to couple to said second member with said second member operative to allow articulation against the femoral area of said patient.

2. The patella replacement device according to claim 1 further comprising:

an annular ring having a central aperture for coupling to said flat surface of said first member and having a plurality of apertures about a periphery of said ring, the periphery surrounding and extending from a peripheral edge of said first member.

3. The patella replacement device according to claim 2 wherein said annular ring is fabricated from a biocompatible metal.

4. The patella replacement device according to claim 3 wherein said metal is titanium.

5. The patella replacement device according to claim 1 wherein said second member is fabricated from polyethylene.

6. The patella replacement device according to claim 1 wherein said second member is fabricated from titanium or cobalt chrome.

7. The patella replacement device according to claim 1 wherein said second member is fabricated from pyrolytic carbon.

8. A patella replacement device for use in repairing or replacing the destroyed natural patella of a patient, comprising:

a first member fabricated from a porous metal material and having a rounded fixation surface for implantation in the patella region of a patient with said porous metal allowing biological fixation to said patella region of said patient, said first member having a relatively flat surface opposite said rounded surface and having at least one aperture therein, a second member fabricated from a biocompatible material and having a top rounded surface and an opposing surface having an extending projection for coacting with said aperture in said first member and dimensional so that a peripheral gap is formed between said first and second member when said projection is inserted into said aperture, said gap enabling the accommodation of soft tissue.

9. The patella replacement device according to claim 8 further comprising:

an annular ring having a central aperture for coupling to said flat surface of said first member and having a plurality of apertures about a periphery of said ring, the periphery surrounding and extending from a peripheral edge of said first member.

10. The patella replacement device according to claim 9 wherein said annular ring is fabricated from a biocompatible metal.

11. The patella replacement device according to claim 10 wherein said metal is titanium.

12. The patella replacement device according to claim 8 wherein said second member is fabricated from polyethylene.

13. The patella replacement device according to claim 8 wherein said second member is fabricated from titanium or cobalt chrome.

14. The patella replacement device according to claim 8 wherein said second member is fabricated from pyrolytic carbon.

15. The patella replacement device according to claim 8 wherein said relatively flat surface of said first member has three apertures, with said second member having three projections each adapted to coact with a respective associated one of said apertures.

16. A patella replacement device for use in repairing or replacing the destroyed natural patella comprising:

a first member fabricated from a porous metal material, said first member having a rounded fixation surface for implantation in the patella region of a patient, and a relatively flat surface opposite said rounded surface, said flat surface having at least one aperture therein;

an annular ring secured about said first member, said ring having a central aperture, an extending flange portion surrounding said first member and a plurality of apertures about a periphery thereof;

a second member fabricated from a biocompatible material having a top round surface and an opposing surface having an extending projection for coacting with said aperture in said first member and dimensioned so that a peripheral gap is formed between said first and second members when said projection of said second member is inserted into said aperture of said first member.

17. The patella replacement device according to claim 16, wherein said annular ring is secured to said first member by an interference fit.

18. The patella replacement device according to claim 16 wherein said annular ring has a peripheral groove about the central aperture thereof.

19. The patella replacement device according to claim 16 wherein said second member is fabricated from polyethylene.

20. The patella replacement device according to claim 16 wherein said annular ring is fabricated from titanium.

21. The patella replacement device according to claim 16 wherein said first member has three apertures on said flat surface.

22. The patella replacement device according to claim 21 wherein said second member has three projections each one operative to coact with an associated one of said three apertures of said first member.

23. The patella replacement device according to claim 22 wherein said second member has a Y-shaped aperture positioned on said opposing surface and located between said projections.

24. The patella replacement device according to claim 16 wherein said porous metal material accommodates a bone cement placed in said at least one aperture.

* * * * *

UNITED STATES PATENT AND TRADEMARK OFFICE
CERTIFICATE OF CORRECTION

PATENT NO. : 6,146,423
DATED : November 14, 2000
INVENTOR(S) : Cohen et al.

It is certified that error appears in the above-identified patent and that said Letters Patent is hereby corrected as shown below:

<u>Title page,</u>
Item [75], please insert -- David Kent DeBoer, Franklin, TN --

Signed and Sealed this

Second Day of April, 2002

*Attest:*

*Attesting Officer*

JAMES E. ROGAN
*Director of the United States Patent and Trademark Office*